United States Patent [19]

Martella et al.

[11] Patent Number: 5,268,524

[45] Date of Patent: Dec. 7, 1993

[54] PREPARATION OF LINEAR ALKYL AROMATICS

[75] Inventors: David J. Martella, Princeton; John J. Jaruzelski, Westfield; Frank J. Chen, Edison, all of N.J.

[73] Assignee: Exxon Chemical Patents Inc., Linden, N.J.

[21] Appl. No.: 950,866

[22] Filed: Sep. 24, 1992

Related U.S. Application Data

[63] Continuation of Ser. No. 595,110, Oct. 10, 1990, abandoned.

[51] Int. Cl.$^5$ ................................................. C07C 2/66
[52] U.S. Cl. ........................................ 585/467; 585/455; 568/797
[58] Field of Search ............... 585/455, 467; 568/797, 568/791

[56] References Cited

U.S. PATENT DOCUMENTS

| | | | |
|---|---|---|---|
| 3,732,324 | 5/1973 | McGuire et al. | 260/671 G |
| 3,917,557 | 11/1975 | Kirk, Jr. | 260/33.6 |
| 4,014,663 | 3/1977 | Feldman et al. | 585/25 |
| 4,033,852 | 7/1977 | Horowitz . | |
| 4,180,691 | 12/1979 | Illingworth | 585/455 |
| 4,224,415 | 8/1980 | Meltzner et al. . | |
| 4,283,573 | 8/1981 | Young . | |
| 4,891,465 | 1/1990 | Tsniguchi et al. | 585/463 |
| 4,912,278 | 3/1990 | Young | 585/458 |
| 4,976,882 | 12/1990 | Martella et al. | 252/48.2 |
| 5,039,437 | 8/1991 | Martella et al. . | |
| 5,082,470 | 1/1992 | Martella et al. | 44/354 |
| 5,118,875 | 6/1992 | Martella et al. . | |

FOREIGN PATENT DOCUMENTS

| | | | |
|---|---|---|---|
| 0029652 | 3/1981 | European Pat. Off. | 585/467 |
| 0988800 | 11/1983 | U.S.S.R. . | |

OTHER PUBLICATIONS

"Alkylation of Aromatics" Kirk Othmer Encyclopedia of Chemical Technology, 3rd Edition, pp. 65–66, Interscience Publishers, Division of John Wiley and Co., N.Y., 1978.

Soviet Inventions Illustrated, section CH, week 8347, Jan. 11, 1984, Derwent Publications Ltd. (London) HO4.

*Primary Examiner*—Anthony McFarlane
*Attorney, Agent, or Firm*—V. T. White

[57] ABSTRACT

Essentially linear alkyl aromatics wherein the alkyl is attached to the aromatic ring at the $\beta$-position are produced by the process wherein a linear hydrocarbon selected from the group consisting of linear $\alpha$-olefins, linear $\alpha$-substituted alkyl halides or linear $\alpha$-substituted alkyl alcohol or mixtures of such olefins, halides or alcohols are reacted with an aromatic compound in the presence of an aprotic-polar cosolvent.

20 Claims, No Drawings

PREPARATION OF LINEAR ALKYL AROMATICS

STATUS OF RELATED APPLICATIONS

This application is a continuation of application Ser. No. 07/595,110, filed Oct. 10, 1990, now abandoned.

The invention relates to an aromatic alkylation process. The invention more specifically relates to an improvement in a process for the alkylation of aromatic hydrocarbons by the introduction thereon of an essentially linear alkyl substituent. The process, therefore, is concerned with the production of aromatic compounds having essentially linear substituents thereon. The invention is, more particularly, concerned with the preparation of alkylated phenol compounds characterized by having essentially linear alkylated substituents thereon.

PRIOR ART

The use of linear alkyl aromatics is known in the art. Linear alkyl aromatics are known as being biodegradable and, therefore, such aromatics particularly converted to detergents through alkylation with subsequent sulfonation, neutralization, etc., result in a more biodegradable detergent. Alkylation of phenols to prepare linear alkylated phenols used in the preparation of phenolsulfur condensates are also known. The alkylation reaction to prepare the essentially linear substituted aromatics have previously been accomplished by a number of techniques which are well known to those skilled in the art. Such methods are, for instance, disclosed in an article entitled "Alkylation of Aromatics", discussed in Kirk Othmer Encyclopedia of Chemical Technology, 3rd edition, Vol. 2, pp. 65–66, Interscience Publishers, Division of John Wiley and Company, New York, 1978, which is incorporated herein by reference.

Several applications, therefore, require preparing essentially linear alkylated aromatics where rearrangements of the alkylating olefins should be minimized. One such application is the preparation of alkylated phenols which are "linear" for use in making alkyl phenol-aldehyde condensates or alkyl phenol-sulfur condensates used as pour point depressants in fuel and lubricating oils. Alkyl phenols are generally prepared by a catalyzed reaction of an olefin with phenol.

U.S. Pat. No. 4,180,691 discloses a hydrocarbon alkylation process and specifically a process for the production of detergent alkylate by the acid-catalyzed alkylation of aromatic hydrocarbon with an olefin in the presence of a surfactant.

Copending U.S. application Ser. Nos. 107,457, filed Oct. 8, 1987, now U.S. Pat. No. 5,976,882 and Ser. No. 107,507, filed Oct. 8, 1987, now U.S. Pat. No. 5,039,437 disclose that in the ideal reaction the olefin forms a carbonium ion species as a result of the presence of acidic conditions and temperature conditions. The cation can then readily react with the substituted aromatic. The cation reacts, for instance, with phenol at either the ortho or para positions.

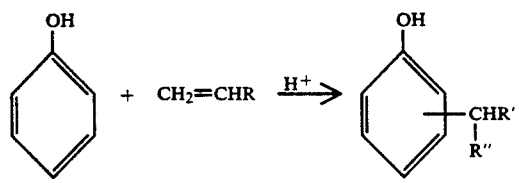

in which reaction R is a linear alkyl and R' an R'' are linear alkyl groups derived in whole or in part from R. The exothermic reaction is thus a simple cationic reaction resulting in a somewhat complex product.

Without rearrangement, the carbonium ion species will attach to the aromatic ring at the beta carbon of the olefin, and R', will thus constitute a pendant methyl group derived from the original olefin, with R'' constituting the remainder of the linear alkyl chain originally defined by R. In reality, however, many side reactions are possible. Thus, the cation can revert back to the olefin or rearrange further down the linear chain, thereby producing attachment to the aromatic ring at a more internal carbon atom and causing the length of R' to increase and R'' to decrease in length correspondingly. It has been found that if these rearrangements are too extensive, they will lead to the production of inferior products which would not suitably interact with the wax crystals of a lubricating oil or fuel oil to which they are eventually added.

It is, therefore, critical to the present invention to minimize these arrangements and to maximize the attachment of the alkyl groups at the 2-position (i.e., beta carbon of the original linear olefin). The instant invention presents a novel method of producing alkyl aromatics having essentially linear alkyl substituted groups. The present invention further describes a method to produce alkyl aromatics and particularly alkyl phenols with less rearrangement, and thereby, for instance, an alkyl phenol-aldehyde or alkyl phenol-sulfur condensate with greater pour point depressancy.

SUMMARY OF THE INVENTION

The invention provides an improved process for the production of linear alkylated aromatics and particularly linear alkylated phenols. The invention comprises reacting an aromatic or substituted aromatic in the presence of an aprotic-polar cosolvent, with a linear alpha-olefin, substituted linear alkyl halides or alcohols or blends of olefins, halides or alcohols.

DETAILED DESCRIPTION

Co-pending applications Ser. No. 07/595,228, filed Oct. 10, 1990, now U.S. Pat. No. 5,118,875 and, application Ser. No. 07/595,229, filed Oct. 10, 1990, now abandoned, and filed, by the same inventors hereto, are directed to preparing alkyl phenol-aldehyde and alkyl-phenol sulfur condensates for use as additives for improving the low temperature flow properties of hydrocarbon oils wherein the alkylation of the phenol is conducted using linear α-olefins.

The present invention is directed to a novel method of preparing "essentially" linear alkylated aromatics and particularly linear alkyl phenols. Essentially linear means greater than 35, preferably at least 40 and most preferably at least 50 mole % of the alkyl groups of the alkylated aromatic are alpha methyl substituted linear alkyl. The primary alkyl aromatic product desired from the alkylation reaction after rearrangement will be linear to at least the above extent.

Alkylation of the aromatic or substituted aromatic compound in accordance with the invention is initially conducted with a linear alpha-olefin, or alpha-substituted olefins such as alkyl halide or alkyl alcohols or a blend of linear alpha olefins, halides or alcohols which are terminal olefins or terminally substituted, as contrasted to internal olefins or internal substitutions. In this manner, it is possible to produce final polymers in which the alkyl group attached to the aromatic ring is essentially linear. "Essentially linear" means that the terminal alpha-olefins, halides or alcohols employed for the alkylation of linear aromatics, and particularly phenols in accordance herewith, will attach to the aromatic ring at the beta carbon thereof, thereby leaving the alpha carbon as a methyl group pendent from the beta carbon of the original olefin or substituted olefin.

The instant invention presents a novel method of producing alkylated aromatics having essentially linear alkyl substituted groups. The novel method involves conducting the alkylation of the aromatic or substituted aromatic in the presence of a polar-aprotic cosolvent or mixtures thereof. The cosolvent of the invention should have a dielectric constant of greater than about 10 and preferably greater than about 20. Typical examples of suitable cosolvents are hexamethylphosphoramide ($e=21$), nitromethane ($e=36$), N-N-dimethylformamide ($e=37$) acetonitrile ($e=36$), sulfolane ($e=44$) and dimethyl sulfoxide ($e=47$). The use of these polar-aprotic cosolvents in the alkylation reaction significantly minimized the amount of rearrangement. The amount of solvent used is not critical and it would be within the knowledge of one skilled in the art to determine suitable amount without undue experimentation. Generally, amounts of above 50 wt. % of the reactant is considered suitable. Amounts, however, greatly in excess of that stated above would not be considered detrimental, but may present problems with removal and would not be cost effective for the process. The minimum amount would be that necessary to produce the desired product.

More specifically, the alkylation process is an acid catalyzed exothermic reaction of the aromatic or substituted aromatic with the linear alpha-olefin, halide or alcohol. The reaction can thus be shown as follows:

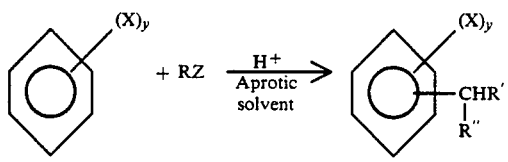

where X can be the same or different and can be an amine, OH, or other functional substituent, an alkyl radical or other functionally substituted alkyl radical of from $C_1$ to $C_{50}$ or mixtures thereof and y is an integer of 0-3. R is an alkyl radical and CH—R″ are alkyls derived in whole or in part from R; and Z is an ethylene radical, halide or hydroxyl. Mixtures of such, of $\alpha$-olefins, $\alpha$-halides or $\alpha$-alcohols are considered to be within the scope of the invention.

The aromatic hydrocarbon used in the process of the instant invention to prepare the "essentially linear" alkylated aromatic hydrocarbon compound are for instance, benzene and alkyl benzenes such as toluene, xylene, ethylbenzene, and phenols, particularly desirable is phenol. Such substituted aromatics can also include aryl alkyl ethers, desirably anisole, anilines, particularly desirable is aniline, and ketones, and most desirable is acetophenone.

The particular linear alpha-olefins, alcohols or halides used in connection with the alkylation step of the present invention are those having the formula RZ, in which R is a straight-chain alkyl having from 4 to 50 carbon atoms. The specific alpha-olefin carbon number found suitable will depend on the intended application.

For instance, the preparation of detergent linear alkyl aromatics a carbon number ranging from about 8 to 22 is generally used. Chlorine is the preferred halide for practicing the invention.

The particular average carbon number range, however, which is most desirable will depend on the ultimate environment intended for the linear alkylated aromatic product. More particularly, it has thus been found that in connection with fuel oils, including diesel fuels and heating oils, to maximize cloud point reduction an average carbon number of about $C_{18}$ is most desired, while to maximize pour point reduction an average carbon number of about $C_{16}$ was most desired. On the other hand, in connection with lubricating oil compositions, the average carbon number for maximizing pour point number reduction was an average carbon content of from about $C_{18}$ to $C_{20}$.

Alkylation reactions can generally be accomplished by a number of acid catalyzed techniques which are well known to those skilled in the art. One particularly suitable technique is by using the Friedel-Crafts reaction which occurs in the presence of a Lewis acid catalyst such as boron trifluoride and its complexes with ethers, hydrogen fluoride, etc., aluminum chloride, aluminum bromide and zinc dichloride, etc.

A particularly preferred catalyst for use in such alkylation reactions is designated Amberlyst 15 by the Rohm and Haas Company. This catalyst is included among the strongly acidic macroreticular resins patented under U.S. Pat. No. 4,224,415. This resin is itself composed of long chains of polystyrene locked together by divinylbenzene crosslinks into a three-dimensional, insoluble polymeric phase called a matrix, on which are attached sulfonic acid groups (—SO$_3$H). Amberlyst 15 possesses high acidity (4.7 meq/g), high porosity (32%) and high surface area (45 m$^2$/g).

In a highly preferred method for carrying out the alkylation reaction as disclosed herein, a zeolite catalyst is employed for use in the selective production of the desired mono-alkylate. More particularly, acidic crystalline zeolites are used which have high silica to alumina ratios and which have effective pore sizes of between about 6 and 8 Angstroms, and include a number of commercial zeolite catalysts, such as LZ-Y82 catalyst manufactured by Union Carbide Corporation. In any event, a general description of these zeolites is set forth in Young, U.S. Pat. No. 4,283,573, which is incorporated herein by reference thereto. In general, these zeolites have a crystal structure which provides access to and egress from the intracrystalline free space of the zeolites by virtue of having channels or networks of pores, the openings of which again preferably have a major dimension, or a free pore diameter, of between about 6A and about 8A. These zeolites are also characterized by pore apertures of about a size as would be provided by 12-member rings of silicon and aluminum atoms. The preferred types of zeolites for use in this invention possess a silica to alumina molar ratio of from about 3:1 to about 6:1. This ratio represents, as closely as possible, the ratio in the rigid anionic framework of the zeolite crystal. Furthermore, these preferred zeolites will have a high surface area, such as about 625 m$^2$/g. The use of these zeolite catalysts thus permits one to eliminate the expensive and difficult distillation step required to separate the mono-alkylate from the di-alkylate produced with the acid-type catalysts previously utilized.

The alkylation process in accordance with the invention is generally conducted at from 50° to 200° C. It is, however, preferred to conduct the alkylation at lower reaction temperatures of 100° C. or below, preferably at or below 90° C. e.g., typically between about 50° C. and 100° C. and preferably between 50° C. and 90° C. to minimize rearrangement. Although the novel process disclosed herein for preparing essentially linear alkylated aromatics can be practiced at higher than the preferred temperatures, it should be evident that the preferred temperature range minimizes rearrangement and optimizes essentially linear attachment to the aromatic ring.

The mode of addition of the reactants and cosolvent is not critical to the preparation of an essentially linear product. Therefore, it is possible to initially simultaneously combine the reactants and cosolvent or to add the aromatic to the olefin, chloride or alcohol containing the catalyst and solvent. The mode of addition is, however, of some importance in the degree of alkylation achieved - multiple linear attachments. The addition of the olefin to the aromatic, for instance, favors monoalkylation whereas simultaneous addition or the addition of the aromatic to the olefin favors polyalkylation. The presence of substituents on the aromatic will, of course, determine where the olefin linear alkyl will attach to the ring. The preferred addition mode for preparing alkylated phenol intermediates used to prepare alkyl phenol aldehyde or alkyl phenol sulfur pour point depressants, for instance, is the addition of the linear alkyl olefin, halide or alcohol to an excess of the aromatic which favors monoalkylation.

The molar ratio of aromatic to olefin, alkyl halide or alkyl alcohol can vary depending on the aromatic being alkylated. Generally, such a ratio can range from 1:1 to about 10:1 (or higher); preferably from about 2:1 to about 5:1. Too great an excess of the aromatic can be disadvantageous because of the need to remove the excess from the product upon completion of the alkylation process.

In connection with an alkylated phenol product, the use of a linear alpha-olefin, alkyl halide or alkyl alcohol or a mixture of linear alpha-olefins, alkyl halides or alkyl alcohols gives a ratio of ortho to para attachments on the phenol of about 2:1. In contrast with the alkylated phenol product of this reaction, the use of a branched internal olefin, mixture of branched internal olefins or internal substituted hydrocarbons gives a ratio of ortho to para attachments on phenol of about 1:18. However, essentially linear alkyl groups attached either ortho or para to the hydroxy groups perform equally well.

The following demonstrates the present invention for producing alkyl phenols with significantly less rearrangement than obtained by current known processes.

EXAMPLE 1

Into a four-neck 1-liter round-bottom flask equipped with a mechanical stirrer, 125 grams of phenol (1.33 moles), 31.5 grams of Amberlyst 15 catalyst, and 164 grams of nitrobenzene were charged. A reflux condenser, a thermometer, an addition funnel and a nitrogen inlet tube were attached to the flask and the mixture was heated to 70° C. With stirring under a blanket of nitrogen, 109 grams (0.43 moles) of 1-octadecene was added dropwise over a period of about one hour. The temperature was raised to 90° C. and maintained at this temperature for four hours. The reaction mixture was then cooled to 50° C. and filtered to remove the catalyst. The excess phenol and nitrobenzene were removed by vacuum distillation. The yield was 207 grams, or 99%. The infrared spectrum of the product showed absorption bands at 830 and 750 cm$^{-1}$, which are characteristic of alkyl phenols. The aromatic substitution pattern was determined by $^{13}$C-NMR spectroscopy and showed that the ortho to para ratio was 1.7:1.0. The alkyl substitution pattern was determined by $^1$H-NMR spectroscopy and showed that the product consisted of 59 mole % 2-substituted alkylate and 41 mole % $\geq$3-substituted alkylate, i.e., 18% less rearrangement than the alkylate produced in accordance with Example 2.

EXAMPLE 2

As an example of the preparation of a typical alkyl phenol component used to produce alkyl phenolformaldehyde condensates, as disclosed in Ser. No. 107,457, filed Oct. 8, 1987, octadecyl phenol was prepared without the cosolvent of the instant invention by charging into a four-neck, 5-liter round-bottom flask equipped with a mechanical stirrer, 933 grams of phenol (9.93 moles) and 286 grams of Amberlyst 15 catalyst. A reflux condenser, a thermometer, an addition funnel, and a nitrogen inlet tube were attached to the flask and the mixture was heated to 70° C. With stirring under a blanket of nitrogen, 834 grams (3.31 moles) of 1-octadecene was added dropwise over a period of about one hour. The temperature was raised to 90° C. and maintained at this temperature for four hours. The reaction mixture was then cooled to 50° C. and filtered to remove the catalyst. The excess phenol was removed by vacuum distillation. The yield was 1,008 grams, or 88%. The product had a refractive index of 1.4859 at 25° C., a viscosity of 38.0 cP at 40° C., and a hydroxyl number of 144 mg KOH/g. The infrared spectrum of the product showed absorption bands at 830 and 750 cm$^{-1}$, which are characteristic of alkyl phenols. The aromatic substitution pattern was determined by $^{13}$C-NMR spectroscopy and showed that the ortho to para ratio was 2.0:1.0. The alkyl substitution pattern was determined by $^1$H-NMR spectroscopy and showed that the product consisted of 50 mole % 2-substituted alkylate and 50 mole % $\geq$3-substituted alkylate.

EXAMPLE 3

In order to demonstrate the criticality of the linearity of the alkyl group with respect to temperature, Example 2 was repeated, except that in this case the mixture was heated to 115° C. instead of 90° C. The yield of octadecyl phenol was 893 grams, or 78%. The product had a hydroxyl number of 138 mg KOH/g, and its infrared spectrum showed absorptions at 830 and 750 cm$^{-1}$, which are characteristic of alkyl phenols. The aromatic substitution pattern was determined by $^1$H-NMR spectroscopy and showed that the product consisted of 35 mole % 2-substituted alkylate and 65 mole % $\geq$3-alkylate. The greater degree of rearrangement in this alkyl phenol was due to the higher reaction temperature.

What is claimed is:

1. An improved method of preparing essentially linear alkylated aromatics comprising contacting, in the presence of at least one polar-aprotic cosolvent or mixture thereof, having a dielectric constant greater than about 10; an aromatic or substituted aromatic compound with an alkylating agent, selected from linear α-olefins, linear α-halides or linear α-alcohols or mixtures thereof, and wherein the alkylating agent has a carbon content of 4 to about 50 carbon atoms.

2. The method of claim 1 wherein the linear α-halide is an alkyl chloride.

3. The method of claim 1 wherein the linear hydrocarbon contains from about 16 to about 20 carbon atoms.

4. The method of claim 1 wherein the polar-aprotic solvent has a dielectric constant greater than 20.

5. The method of claim 4 wherein the dielectric constant of the polar-aprotic solvent ranges from about 10 to about 50.

6. The method of claim 1 wherein the polar-aprotic solvent is selected from the group consisting of nitrobenzene, nitromethane; N,N-dimethylformamide acetonitrile; sulfolane and dimethyl sulfoxide.

7. The method of claim 6 wherein the polar-aprotic solvent is nitrobenzene.

8. The method of claim 1 wherein the alkylation is conducted in the presence of an acidic catalyst.

9. The method of claim 8 wherein the alkylation is conducted in the presence of an acidic crystalline aluminasicilate zeolite catalyst.

10. The method of claim 9 wherein the zeolite catalyst has a silica to alumina ratio of about 3:1 to about 6:1.

11. The method of claim 1 wherein the aromatic has the formula:

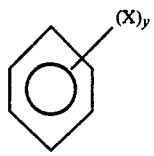

wherein X can be the same or different and is selected from amines, OH, an alkyl radical or functionally substituted alkyl radical having 1–50 carbon atoms or mixtures thereof, and y is o or an integer of from 1–3.

12. The method of claim 11 wherein the aromatic is benzene.

13. The method of claim 11 wherein the substituted aromatic is a phenol.

14. The method of claim 11 wherein the substituted aromatic is xylene.

15. The method of claim 1 wherein the molar ratio of aromatic to linear hydrocarbon ranges from about 1:1 to 10:1.

16. The method of claim 15 wherein the molar ratio is from about 2:1 to 5:1.

17. The method of claim 13 wherein the molar ratio of phenol to olefin is less than about 3:1.

18. The method of claim 1 wherein the linear hydrocarbon ranges from $C_{18}$ to $C_{20}$.

19. The method of claim 1 wherein the alkylation is conducted at a temperature of from about 50° C. to 200° C.

20. The method of claim 15 wherein the alkylation is conducted below 100° C.

* * * * *